(12) United States Patent
Kismarton

(10) Patent No.: US 7,807,249 B2
(45) Date of Patent: Oct. 5, 2010

(54) COMPOSITE ARTICLE HAVING REINFORCING FIBERS ORIENTED TO SUPPRESS OR DELAY PLY SPLITTING

(75) Inventor: Max U. Kismarton, Renton, WA (US)

(73) Assignee: The Boeing Company, Chicago, IL (US)

(*) Notice: Subject to any disclaimer, the term of this patent is extended or adjusted under 35 U.S.C. 154(b) by 104 days.

(21) Appl. No.: 12/340,631

(22) Filed: Dec. 19, 2008

(65) Prior Publication Data

US 2009/0104398 A1   Apr. 23, 2009

Related U.S. Application Data

(63) Continuation-in-part of application No. 11/096,727, filed on Mar. 31, 2005, now abandoned.

(51) Int. Cl.
*B32B 9/00* (2006.01)

(52) U.S. Cl. .............. 428/113; 428/293.1; 156/243
(58) Field of Classification Search ............... 428/113, 428/292.1, 293.1; 52/831, 837, 841; 156/243
See application file for complete search history.

(56) References Cited

U.S. PATENT DOCUMENTS

| | | | | | |
|---|---|---|---|---|---|
| 1,942,354 | A | * | 1/1934 | Collings et al. | 428/108 |
| 2,126,837 | A | * | 8/1938 | Stewart et al. | 105/15 |
| 2,338,447 | A | * | 1/1944 | Lenart et al. | 474/271 |
| 2,631,957 | A | * | 3/1953 | Francis, Jr. | 428/297.7 |
| 2,834,702 | A | * | 5/1958 | Gibb | 220/562 |
| 2,912,849 | A | * | 11/1959 | Wissinger | 52/606 |
| 2,977,270 | A | * | 3/1961 | Bodle | 156/270 |

* cited by examiner

*Primary Examiner*—N. Edwards

(57) ABSTRACT

A composite article comprises a plurality of reinforcing fibers embedded in a matrix. The fibers have a fiber orientation of ±α with respect to an axis of loading, where α=2 to 8 degrees to suppress or delay ply splitting.

20 Claims, 3 Drawing Sheets

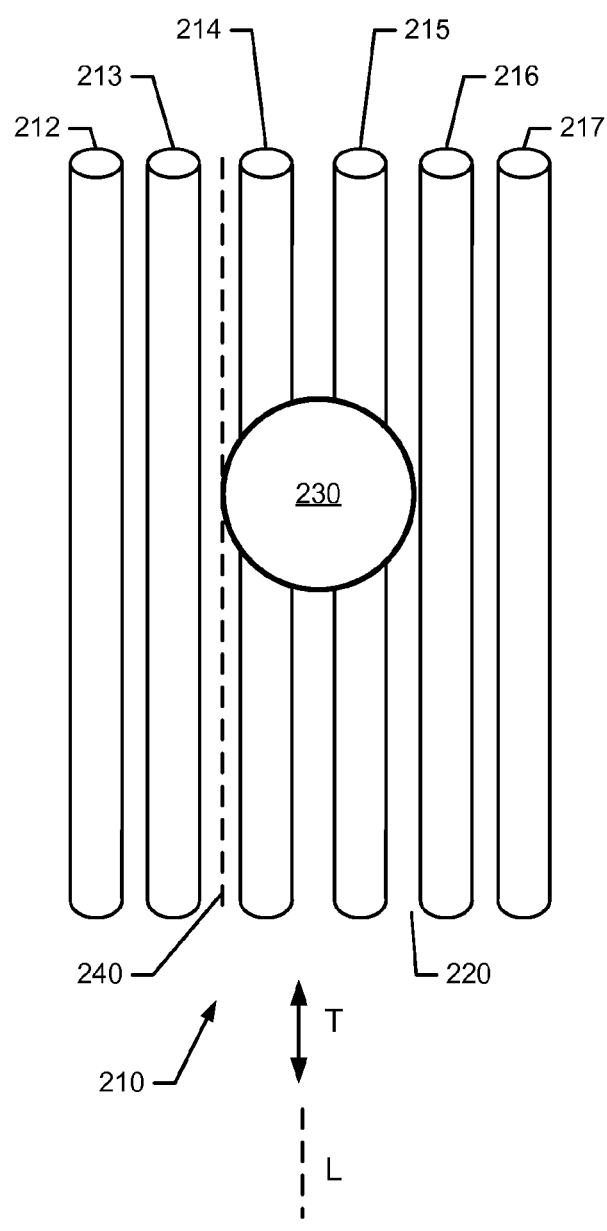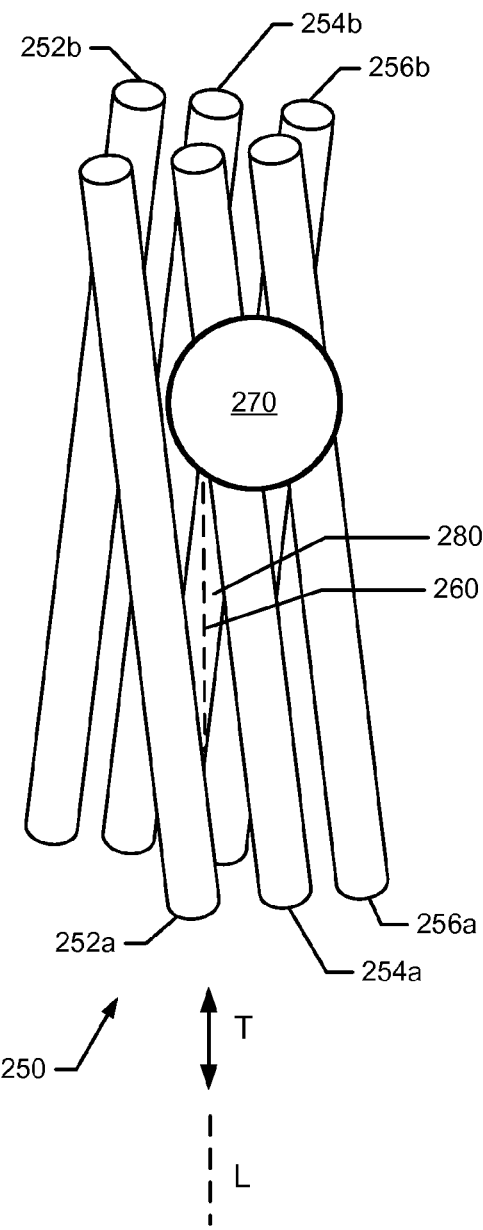

COMPOSITE ARTICLE HAVING REINFORCING FIBERS ORIENTED TO SUPPRESS OR DELAY PLY SPLITTING

BACKGROUND

Articles made of a composite material such as carbon fiber reinforced plastic (CFRP) may include multiple plies of reinforcing fibers at different fiber orientations. Reinforcing fibers in some plies may be oriented at 0 degrees for strength in tension and compression. Reinforcing fibers in other plies may be oriented at other angles (+45 degrees, −45 degrees, 90 degrees) for shear and bearing strength.

SUMMARY

According to an embodiment herein, a composite article comprises a plurality of reinforcing fibers embedded in a matrix. The fibers have an orientation of ±α with respect to an axis of loading, where α=2 to 8 degrees for suppression or delay of ply splitting.

According to another embodiment herein, a method of manufacturing a composite article comprises laying up plies of reinforcing fibers on a tool. The fibers in at least some of the plies have an orientation of ±α with respect to a uni-axial load bearing direction of the article, where α=2 to 8 degrees.

According to another embodiment herein, a method of manufacturing a composite article comprises creating a laminate of reinforcing fibers embedded in a matrix. The fibers have an orientation of ±α with respect to a uni-axial load bearing direction of the article. The method further comprises machining at least some of the fibers. The fiber orientation of ±α suppresses or delays ply splitting in the composite article when the article is loaded in compression or tension.

BRIEF DESCRIPTION OF THE DRAWINGS

FIG. 2a is an illustration of fibers oriented at 0 degrees with respect to an axis of loading.

FIG. 2b is an illustration of fibers oriented at ±α degrees with respect to an axis of loading.

DETAILED DESCRIPTION

Figure 1:
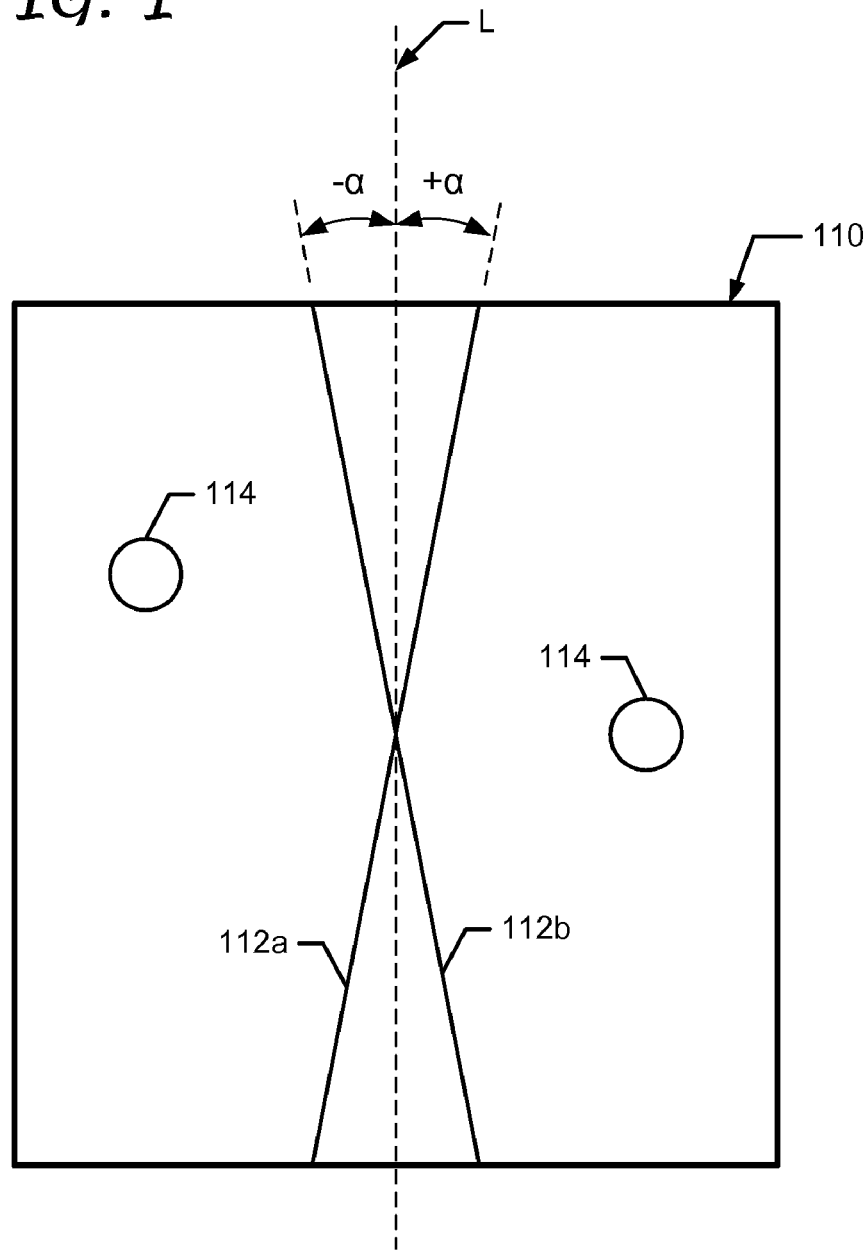
FIG. 1 is an illustration of a composite article.

Reference is made to FIG. 1, which illustrates a composite article 110. The composite article 110 includes a plurality of reinforcing fibers 112a and 112b embedded in a matrix. The fibers 112a have a fiber orientation of +α with respect to an axis L of loading, and the fibers 112b have a fiber orientation of −α with respect to the axis L. Thus, the fibers 112a and 112b are said to have a fiber orientation of ±α with respect to the axis L. The value of α is between 2 and 8 degrees. The fiber orientation of ±α unexpectedly suppresses or delays ply splitting.

The article 110 may be uni-axially loaded along the axis L. The article 110 may also have twist and transverse loading during usage. Still, the fibers 112a and 112b are oriented at ±α with respect to the axis L.

For clarity, only two reinforcing fibers 112a and 112b are illustrated in FIG. 1. The article 110 has many more reinforcing fibers 112a and 112b oriented at +α and −α.

The article 110 may be a laminate of multiple plies of reinforcing fibers, where one or more of those plies have fibers 112a and 112b oriented at ±α. In some embodiments, a single ply may have fibers 112a and 112b oriented at +α and −α.

In other embodiments, the fibers 112a or 112b in each ply are unidirectional. For instance, an article 110 includes a first ply having fibers 112a oriented at +α degrees, a second ply having fibers 112b oriented at −α degrees, a third ply having fibers 112a oriented at +α degrees, a fourth ply having fibers 112b oriented at −α degrees, and so on.

The article 110 may be machined. As a first example, a hole 114 is drilled into the article 110. The hole 114 cuts through a plurality of fibers 112a and 112b. As a second example, an end of the article 110 is saw cut. This cut exposes the ends of a plurality of fibers 112a and 112b.

If fibers 112a and 112b in the article 110 are cut and the article 110 is loaded uni-axially along the axis L (e.g., the article is placed in tension or compression along the axis L), the splitting of the ply will be suppressed or delayed relative to a hard laminate having a majority of fibers oriented at 0 degrees.

Reference is now made to FIGS. 2a and 2b, which illustrate matrix splitting for fibers oriented at 0 degrees and ±α, respectively. FIG. 2a illustrates a single ply 210 having six fibers 212-217 embedded in a matrix 220. The fibers 212-217 are oriented at 0 degrees with respect to axis L. Fibers 214 and 215 are cut by drilling a hole 230. When a tensile load is applied along axis L, the uncut fibers 212-213 and 216-217 carry the load and stretch. The cut fibers 214-215 do not carry the load, do not stretch, and are sheared away from the matrix 220. This, in turn, weakens the ply 210 between a cut fiber 214 and an uncut fiber 213. A slender crack 240 (represented by the dash line) forms in the ply 210 between the cut and uncut fibers 214 and 213. This crack 240 can propagate along the entire length of the ply 210. The crack 240 can occur whether an article has one ply, five plies, tens plies, or more. The crack 240 degrades the strength of the article.

FIG. 2b illustrates a layer 250 of fibers 252a-256a oriented at −α with respect to axis L, and fibers 252b-256b oriented at +α with respect to the axis L. The layer 250 may include a single ply having fibers 252a-256a and 252b-256b or two unidirectional plies (one unidirectional ply having fibers 252a-256a and another unidirectional ply having fibers 252b-256b). If fibers 254a, 256a, 254b and 256b are cut by a hole 270, a small crack 280 will form in the layer 250, but the crack 280 will not grow in an uncontrolled manner. Instead, growth of the crack 280 will slow and eventually stop, whereby strength of the article is retained. Moreover, due to the fiber orientation at ±α, a higher load will be needed to initiate the crack 280 (the angled fibers are believed to diffuse the load). Ply splitting will be suppressed or delayed.

An angle α in the range of 2 to 8 degrees provides a good combination of strength and splitting suppression. For angles α exceeding 8 degrees, strength drops off quickly. For angles below 2 degrees, ply splitting increases rapidly.

An angle α in the range of 3-5 degrees provides a better combination of strength and splitting suppression/delay, and it also provides a margin of error against strength drop-off which can occur below α=2 degrees and above α=8 degrees (if fiber control is insufficient during fabrication, some fibers might be oriented at angles less than 2 degrees or greater than 8 degrees). An angle α of 3 degrees has been found to provide an even better combination, as it provides 1-2% more strength in compression.

However, the optimal angle for α will usually be a function of several factors. These factors include, but are not limited to, the fiber, the matrix, interface bonding strength between a fiber and the matrix, fiber density, fiber length, etc. These factors also include the ability to control fiber orientation.

The reinforcing fibers and matrix are not limited to any particular composition. Examples for the fibers include, but are not limited to, carbon, fiberglass, Kevlar, boron, or titanium. Examples for the matrix include, but are not limited to, plastic and metal. As a first example, carbon fibers are embedded in a plastic matrix. As a second example, carbon fibers are embedded in a titanium matrix.

The article 110 is not limited to any particular cross-section. Without limitation, the cross-section could be rectangular, square, I-beam, etc.

In some embodiments, the article 110 may only have reinforcing fibers oriented at ±α. That is, the article 110 has 100% reinforcing fibers at ±α.

The article may also be provided with a means for increasing strength or stiffness in at least one of shear, transverse and bearing. In some embodiments, the means may include a metal foil on the composite article.

In other embodiments, the article 110 may have additional fibers oriented at different angles to provide strength in shear and bearing. As a first example, additional reinforcing fibers are oriented at a conventional 45 degrees and 90 degrees.

As a second example, additional reinforcing fibers are oriented at ±β, where β is between 50 and 85 degrees (e.g., ±55, ±60, ±65, ±70, ±75). Fibers at ±β unexpectedly boost shear, transverse and bearing strength. For instance, fibers at ±β can be added to boost bearing strength in areas where fasteners are used to make a fastened joint or repair a joint. Since fewer plies are need for fibers at ±β (that is, relative to fibers oriented at 90 degrees, +45 degrees and −45 degrees), the resulting article is more usable, tailorable, efficient and lighter.

Selective fiber orientation allows any of six characteristics to be adjusted: strength in shear, stiffness in shear, strength in transverse, stiffness in transverse, bearing strength, and bearing stiffness. If greater strength in shear is desired, a β approaching 50 degrees will be selected. If greater strength in transverse is desired, a β approaching 85 degrees will be selected. If greater strength in bearing is desired, a β approaching 65-70 degrees will be selected.

Of the total fibers oriented at ±α and ±β, only 20-30% of the total fibers at ±β are needed to reach bearing strength levels similar to traditional 0/+45/−45/90 degree plies. However, unlike traditional laminates, ply splitting will be suppressed or delayed if fibers in the article are cut and loaded.

In some embodiments, plies of the fibers oriented at ±β may be interspersed with plies of the fibers oriented at ±α. Consider an example of unidirectional plies that are interspersed. The plies may have the following order: +α/−α/+β/+α/−α/−β/+α/−α/. That order (having fibers +β and −β near the inside of the article) would allow greater transverse bending than an order in which the plies have fibers +β and −β toward the outside of the article.

Figure 3:
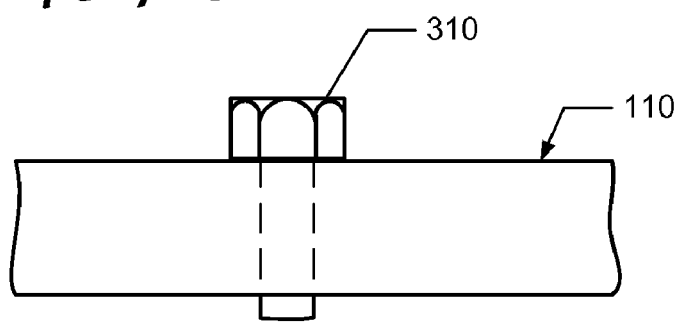
FIG. 3 is an illustration of a fastener extending through a composite article.

Reference is made to FIG. 3, which shows a fastener 310 extending through a fastener hole in the an article 110. Examples of fasteners 310 include, without limitation, bolts and rivets. Fibers oriented at ±β boost bearing strength in areas where the fastener 310 extends through the article 110.

Figure 4:
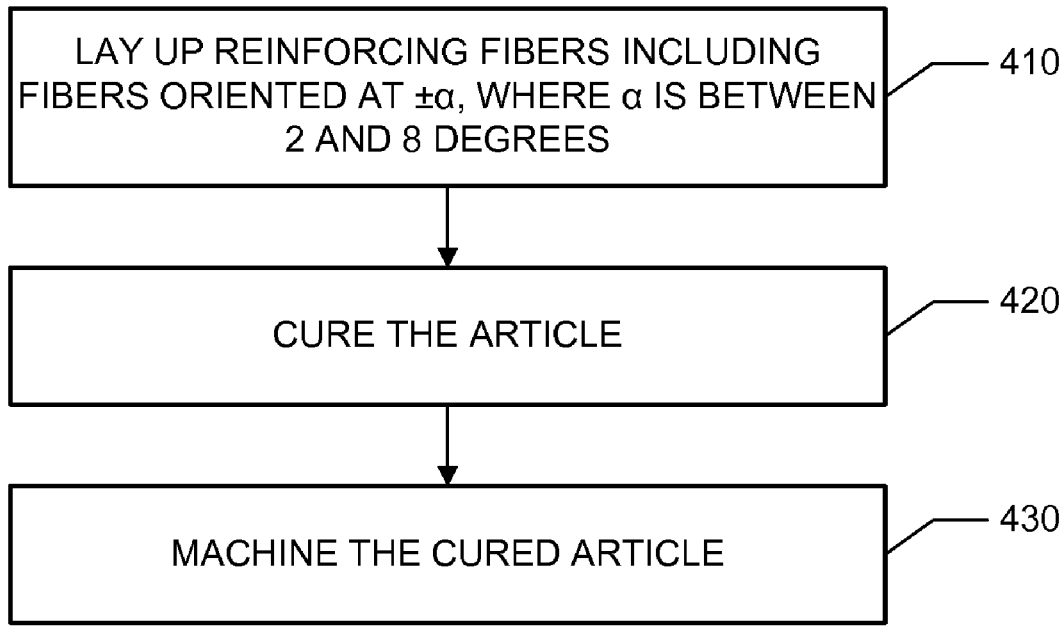
FIG. 4 is an illustration of a method of fabricating a composite article.

Reference is now made to FIG. 4, which illustrates a method of manufacturing a composite article. At block 410, one or more plies of reinforcing fibers are laid up on a tool (e.g., mandrel or mold tool). The lay-up includes laying up plies of fibers at +α and −α. The lay-up may also include laying up plies of fibers at other angles, such as +β and −β.

As a first example, only plies of fibers at ±α are laid up. As a second example, one or more plies at ±α and ±β may be laid up. Of the total fibers oriented at ±α and ±β, only 20% of fibers at ±β may be used to reach bearing strength levels similar to traditional 0/45/90 deg plies in the lengthwise direction.

In some embodiments, each ply may be a unidirectional tape with fibers oriented at 0 degrees with respect to a longitudinal axis of the tape. These tapes are dispensed on the tool and rotated to the correct angle (e.g., +α). As a result, some of the tape may overhang the tools. The overhanging portions can eventually be cut off (for instance, after curing).

In other embodiments, "cartridges" may be laid up. Cartridges may include pre-packaged plies having the correct fiber orientation (e.g., +α and −α) with respect to the cartridge's longitudinal axis. Such cartridges can be dispensed on the tool without overhang. For example, the cartridge can be dispensed with its longitudinal axis parallel to the longitudinal axis of the tool.

In some embodiments, a cartridge may include two plies that are stitched together. One ply may have fibers oriented at +α and the other ply may have fibers oriented at −α. Both plies have the correct fiber orientation with respect to the cartridge's longitudinal axis.

The fibers may be balanced or slightly unbalanced. As an example of balanced fibers, an article has N plies of fibers at +α interspersed with N plies of fibers at −α. As an example of slightly unbalanced fibers, an article may have N plies of fibers at +α interspersed with N−1 plies of fibers at −α.

In some embodiments, all plies may have the same +α and the same −α. In other embodiments, the fibers may have different values of α. For instance, reinforcing fibers having orientations of α=3 degrees and α=5 degrees may be laid up.

In some embodiments, a ply may have fibers at different angles. For example, a ply may include fibers oriented at angles of −3 degrees, +7 degrees, −7 degrees, and +2 degrees.

In some embodiments, a weave may be dispensed instead of unidirectional tape. Unlike tapes, which have no crimp, the fibers in weaves are crimped. And unlike tapes, a single wave can have fibers oriented at +α and fibers oriented at −α.

At block 420, the article is cured. A matrix (e.g., a thermoplastic or thermoset) can be added before, after or while the plies are either laid up or being cured.

At block 430, the article is machined. For example, fastener holes or other types of holes may be drilled into the cured composite article. The holes may be drilled while the article is on the tool, or after the article has been removed from the tool. The holes may be roughly perpendicular to the plies.

Figure 5:
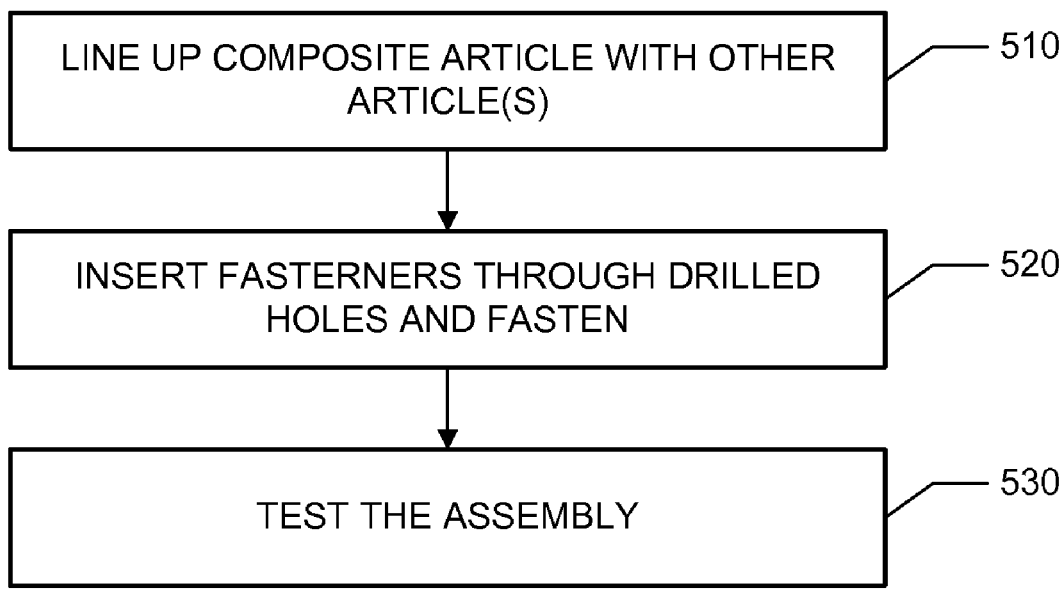
FIG. 5 is an illustration of a method of assembling a composite article.

Reference is now made to FIG. 5. The composite article is assembled to at least one other article, which may or may not be made of composite material. At block 510, holes in the articles are lined up. At block 520, fasteners are inserted through holes, and the articles are fastened together.

At block 530, the assembly undergoes testing or goes into service. The testing may be static or dynamic, or both.

The invention claimed is:

1. A composite article comprising a plurality of reinforcing fibers embedded in a matrix, the fibers having a fiber orientation of ±α with respect to an axis of loading, where α=2 to 8 degrees for suppression or delay of ply splitting.

2. The article of claim 1, wherein the article is designed to be uni-axially loaded along the axis.

3. The article of claim 1, wherein α=3 to 5 degrees.

4. The article of claim 1, wherein α=3 degrees.

5. The article of claim 1, wherein at least some of the reinforcing fibers at ±α are machined.

6. The article of claim 1, further comprising drilled holes through at least some of the fibers.

7. The article of claim 6, further comprising fasteners extending through the drilled holes.

8. The article of claim 1, wherein the article includes a laminate of multiple plies of the fibers.

9. The article of claim 8, wherein the fibers provide strength in compression and tension, and wherein the article further comprises means for providing additional strength in at least one shear, transverse and bearing.

10. The article of claim 9, wherein the means includes at least one ply having fibers oriented at ±β, where β is between 50 and 85 degrees.

11. The article of claim 10, wherein of the total fibers oriented at ±α and ±β, only 20-30% of the total fibers are oriented at ±β.

12. A method of manufacturing a composite article comprising laying up plies of reinforcing fibers on a tool, wherein the fibers in at least some of the plies have an orientation of ±α with respect to a uni-axial load bearing direction of the article, where α=2 to 8 degrees.

13. The method of claim 12, wherein each ply includes unidirectional fibers having a 0 degree orientation, wherein the plies are rotated to their correct angles of ±α while being dispensed on the tool, and wherein overhang is afterward cut off.

14. The method of claim 12, wherein cassettes having fibers oriented at ±α are dispensed on the tool.

15. The method of claim 14, wherein each cassette includes a first ply having fibers oriented at +α and a second ply having fibers oriented at −α, the first and second plies bound together.

16. The method of claim 12, wherein the fibers in at least some of the plies have an orientation to boost shear, transverse and bearing strength.

17. The method of claim 16, wherein the fibers for boosting shear, transverse and bearing strength are oriented at ±β, where β is between 50 and 85 degrees.

18. A method of manufacturing a composite article, comprising creating a laminate of reinforcing fibers embedded in a matrix, the fibers having an orientation of ±α with respect to a uni-axial load bearing direction of the article; and machining at least some of the fibers, the fiber orientation suppressing or delaying ply splitting in the composite article when the article is loaded in tension or compression.

19. The method of claim 18, wherein at least some of the fibers are cut by drilling a hole into the laminate.

20. The method of claim 19, wherein α=3 to 5 degrees.

* * * * *